United States Patent [19]

Spivack

[11] Patent Number: 5,211,862
[45] Date of Patent: May 18, 1993

[54] SUBSTITUTED N-THIOMETHYLPHENOTHIAZINES AS LUBRICANT STABILIZERS

[75] Inventor: John D. Spivack, Spring Valley, N.Y.

[73] Assignee: Ciba-Geigy Corporation, Ardsley, N.Y.

[21] Appl. No.: 481,771

[22] Filed: Feb. 16, 1990

Related U.S. Application Data

[63] Continuation of Ser. No. 315,257, Feb. 21, 1989, abandoned, which is a continuation of Ser. No. 948,272, Dec. 31, 1986, abandoned.

[51] Int. Cl.$^5$ .......................................... C10M 135/36
[52] U.S. Cl. ...................................... 252/47.5; 252/47; 208/18
[58] Field of Search .................. 252/47, 47.5, 56 S; 208/18; 544/38; 524/83

[56] References Cited

U.S. PATENT DOCUMENTS

| | | | |
|---|---|---|---|
| 2,781,318 | 2/1957 | Cyphers | 252/47 |
| 3,014,888 | 12/1961 | Shimmin et al. | 252/47 |
| 3,038,858 | 6/1962 | Verley | 252/47 |
| 3,218,256 | 11/1965 | Edwards | 252/47 |
| 3,344,068 | 9/1967 | Waight | 252/47 |
| 3,376,224 | 4/1968 | Elliott et al. | 252/47.5 |
| 3,389,124 | 6/1968 | Sparks | 252/47 |
| 3,494,885 | 2/1970 | Thompson | 524/83 |
| 3,523,910 | 8/1970 | Randell | 252/47 |
| 3,535,243 | 10/1970 | Chao et al. | 252/51.5 A |
| 3,536,706 | 10/1970 | Randell et al. | 260/243 |
| 4,072,619 | 2/1978 | Williams et al. | 252/47 |
| 4,510,041 | 4/1985 | Miller et al. | 252/47 |
| 4,785,095 | 11/1988 | Salomon | 544/38 |

OTHER PUBLICATIONS

Winthrop et al, J.A.C.S., 80, 4331–33 (1958).

*Primary Examiner*—Margaret Medley
*Attorney, Agent, or Firm*—Luther A. R. Hall; Harry Falber

[57] ABSTRACT

Lubricants stabilized against oxidative degradation by the incorporation therein of N-thiomethylphenothiazine derivatives, as well as certain phenothiazines within the indicated group.

6 Claims, No Drawings

SUBSTITUTED N-THIOMETHYLPHENOTHIAZINES AS LUBRICANT STABILIZERS

This application is a continuation of application Ser. No. 315,257, filed Feb. 21, 1989, now abandoned, which is a continuation of Ser. No. 948,272, filed Dec. 31, 1986, now abandoned.

This invention relates to lubricant compositions which are stabilized against oxidative degradation by the presence therein of certain N-thiomethylphenothiazine derivatives. It also relates to a number of novel phenothiazines within the broader group.

It is known to stabilize lubricants by the addition of antioxidants such, for example, as sterically hindered phenols, derivatives of p-phenylene diamine or of diphenylamine in order to avoid decomposition, sludge formation, viscosity increases, and the like. U.S. Pat. No. 3,535,243 also discloses the use of diaminonaphthalenes as antioxidative additives for ester lubricants, while U.S. Pat. No. 3,536,706 discloses N-unsubstituted phenothiazines for a similar purpose.

It has now been discovered that certain derivatives of N-thiomethylphenothiazine show surprisingly high stabilizer activity and sufficient solubility in a broad range of mineral and synthetic oils. Thus, the subject matter of the instant invention is a lubricant composition comprising mineral oils, synthetic oils, mixtures thereof, and the like, and an antioxidative compound corresponding to the formula

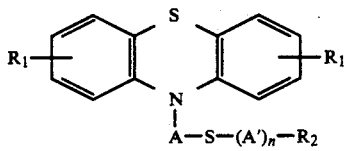

wherein $R_1$ are independently hydrogen, alkyl of 1 to 24 carbon atoms, cycloalkyl of 5 to 7 carbon atoms or aralkyl of 7 to 9 carbon atoms;

A and A' are independently alkylene of 1 to 8 carbon atoms;

n is 0 or 1; and $R_2$ is alkyl of 1 to 18 carbon atoms, cycloalkyl of 5 to 7 carbon atoms, said cycloalkyl substituted by alkyl of 1 to 18 carbon atoms, phenyl, phenyl substituted by alkyl, alkoxy or thioalkyl to a total carbon atom content of 7 to 30, naphthyl or naphthyl substituted by alkyl, alkoxy or thioalkyl to a total carbon atom content of 11 to 40.

Alkyl groups within the indicated definitions may be straight-chain or branched and may be methyl, ethyl, propyl, isopropyl, n-butyl, isobutyl, n-hexyl, n-octyl, 2-ethylhexyl, n-decyl, n-dodecyl, n-octadecyl or n-eicosyl. Cycloalkyl may be cyclopentyl or cyclohexyl. Aralkyl may be benzyl, α-methylbenzyl or α,α-dimethylbenzyl.

Alkylene groups include methylene, propylene, hexylene or octylene, but preferably correspond to the formula

wherein $R_3$ is alkyl of 1 to 7 carbon atoms.

Preferred compounds include those wherein $R_1$ are independently hydrogen or alkyl of 1 to 12 carbon atoms; A and A' are independently

and $R_2$ is alkyl of 4 to 12 carbon atoms or phenyl or phenyl mono- or di- or trisubstituted by alkyl of 1 to 8 carbon atoms or with one of the substituents being alkoxy or thioalkyl of 1 to 12 carbon atoms.

The N-thiomethylphenothiazine compounds may be prepared by reacting phenothiazine, formaldehyde and the appropriately substituted mercaptan or thiophenol in the presence of an alcoholic solvent such as methanol and ethanol at reaction temperatures ranging from 25° to 200° C. The various starting materials needed to prepare the indicated compounds are items of commerce or can be prepared by known methods.

The lubricant may be an oil or a grease based on mineral or synthetic oils, these lubricants being well known to those skilled in the art. The term mineral oil includes all mineral oils used for lubricant purposes, such as hydrocarbon mineral oils. The synthetic oil may be, for instance, an aliphatic or aromatic carboxylic ester, a polymeric ester, a polyalkylene oxide, a phosphoric acid ester, polyalphaolefins, or a silicone. Greases may be obtainable from these by adding metal soaps or similar thickeners.

The amount of phenothiazine compound added to the lubricant depends on the sensitivity of the oil base to oxidation and on the desired degree of protection. Generally, 0.01 to 2% by weight will be added, and preferably 0.05 and 0.5%. The compounds may be used in combination with other antioxidants known as oil additives. Examples thereof are aromatic amines such as p-tert.octylphenyl-α-naphthylamine, p,p'-di-tert.octyldiphenylamine, 2,3-dihydro-3,3-dimethyl-4H-1,4-benzothiazine, phenothiazine, diphenylamine, N-allylphenothiazine, N-allyldiphenylamine or phenyl-α(β)naphthylamine; hindered phenols such as neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris-(3,5-di-tert-butyl-4-hydroxybenzyl)benzene, 1,3,5-tris-(3,5-di-tert-butyl-4-hydroxybenzyl)isocyanurate, 2,6-di-tert-butyl-p-cresol or 2,2'-ethylidene-bis(4,6-di-tert-butylphenol; aliphatic or aromatic phosphites; esters of thiodipropionic or thiodiacetic acid; or salts of dithiocarbamic or dithiophosphoric acids.

Such antioxidant combinations may show a synergistic action, i.e., the stabilizing effect of such a mixture being greater than the sum of the performances of the individual antioxidants. Such synergistic performance can be obtained when combining the instant compounds with certain aromatic amines or hindered phenols or with both types of antioxidants.

The lubricant composition may also contain other additives, such as metal-passivating agents including 5,5'-methylene-bisbenzotriazole, 4,5,6,7-tetrahydrobenzotriazole and 2,5-dimercaptothiadiazole; rust inhibitors; viscosity regulators including polyacrylates, polybutenes, polyvinylpyrrolidones and polyethers; pour point depressants; dispersing agents; detergents; or extreme pressure/anti-wear agents including triphenyl phosphorothionates, diethanolaminomethyl tolyltriazole and di(2-ethylhexyl)aminomethyl tolyltriazole; said additives being widely known and used in lubricants.

Phenothiazine compounds within the generic formula wherein $R_2$ is alkyl have been previously disclosed. For example, U.S. Pat. No. 3,494,885 discloses N-substituted phenothiazines wherein the N-substitution is $C_2$–$C_{18}$ alkylenethioalkyl for use as antioxidants in polycarbonates and polyesters. Similarly N-alkylenethioalkylphenothiazines have been disclosed in Winthrop et al, J. Am. Chem. Soc., 80, 4331–33 (1958) for a pharmacological utility.

Accordingly, the novel phenothiazines forming part of the instant invention correspond to the above noted generic formula with the exception that the $R_2$ definition does not include alkyl. The preferred substituents are also as defined above, excepting $R_2$ as alkyl, and the methods of preparation are, of course, as described hereinabove.

Compounds of this invention are also effective in stabilizing other organic materials such as plastics, polymers and resins in addition to the mineral and synthetic fluids.

Substrates in which the compounds of this invention are particularly useful are polyolefins such as polyethylene and polypropylene, polystyrene, including impact polystyrene, ABS resin, SBR, isoprene, as well as natural rubber; polyesters including polyethylene terephthalate and polybutylene terephthalate, including copolymers.

These stabilized polymer compositions may optionally also contain various conventional additives such as antioxidants including alkylated monophenols, alkylated hydroquinones, hydroxylated thiodiphenyl ethers, alkylidene-bisphenols, various benzyl compounds, acylaminophenols and esters and amides of hindered hydroxyphenyl propionic acids; UV absorbers and light stabilizers including hydroxyphenyl benzotriazoles, benzophenones, benzoic acid esters, acrylates, nickel compounds, sterically hindered amines and oxalic acid diamides.

The following examples will further illustrate the embodiments of the instant invention.

EXAMPLE I

N-(Phenyliomethylene)phenothiazine

Phenothiazine (19.9 grams, 0.100 mol) is dispersed in 150 ml of ethanol and benzenethiol (11.4 grams, 0.101 moles) is added to the dispersion followed by 37.4% formaldehyde (8.9 grams, 0.111 moles).

The dispersion is heated for 24 hours, further heating indicating that no additional reaction is taking place. The solvent is removed by distillation at 20 mm Hg pressure and unreacted benzenethiol removed at reduced pressure. The residue (28 grams) is crystallized successively from n-heptane, and a mixture of ethanol-cyclohexane yielding a total of 14.6 grams (45% yield) of the desired product as white crystals.

Anal. Calcd. for $C_{19}H_{15}NS_2$: C, 70.99; H, 4.70; N, 4.36. Found: C, 70.8; H, 4.7; N, 4.3

EXAMPLE II

N-(n-Octylthiomethylene)phenothiazine

Formaldehyde (37 wt. %, 6.9 grams, 0.111 moles) is added to a dispersion of phenothiazine (19.9 grams, 0.100 moles) in 250 ml. of methanol, n-Octyl mercaptan (15.0 grams, 0.100 moles) is then added and the mixture stirred at reflux for about 30 hours. The solvent is removed at reduced pressure and the resulting residue dissolved in 400 ml of toluene and washed with water and dried over sodium sulfate. The dried toluene solution is freed of solvent under pressure with the residue being dissolved in 150 ml of refluxing n-heptane and allowed to cool to room temperature. Thin layer chromatography shows the crystalline precipitate (6.8 grams) to be phenothiazine. Removal of the heptane by distillation of the n-heptane under vacuum yields 25.6 grams of a brown residual liquid. This residual liquid is purified by High Pressure Liquid Chromatography, yielding 18.2 grams of yellow liquid (51% yield).

Anal. Calcd. for $C_{21}H_{27}NS_2$: C, 70.54; H, 7.61; N, 3.92; S, 17.93. Found: C, 70.4; H, 7.9; N, 4.1; S, 17.8

EXAMPLE III

N-(Benzylthiomethylene)phenothiazine

The compound of Example III is prepared by following the general procedure of Example I and reacting benzylthiol with formaldehyde and phenothiazine.

EXAMPLE IV

N-(4-Tert-butylphenylthiomethylene)phenothiazine

The compound of Example IV is prepared by following the general procedure of Example I and reacting 4-tert-butylthiophenol with formaldehyde and phenothiazine.

EXAMPLE V

N-(2,4-Dimethylphenylthiomethylene)phenothiazine

The compound of Example V is prepared by following the general procedure of Example I and reacting 2,4-dimethylthiophenol with formaldehyde and phenothiazine.

EXAMPLE VI

N-(4-Methoxyphenylthiomethylene)phenothiazine

The compound of Example VI is prepared by following the general procedure of Example I and reacting 4-methoxythiophenol with formaldehyde and phenothiazine.

EXAMPLE VII

N-(2-Naphthylthiomethylene)phenothiazine

The compound of Example VII is prepared by following the general procedure of Example I and reacting 2-naphthylmercaptan with formaldehyde and phenothiazine.

EXAMPLE VIII

Engine Oil Thin Film Oxygen Uptake Test

This test is conducted in a standard rotary bomb apparatus (described in ASTM D-2272) with modifications in procedure as described in the Preprint No. 82 CC-10-1, presented at the Conference of the American Society of Lubrication Engineers, Oct. 5–7, 1982.

A 1.5 ml. test sample of 150 N paraffinic mineral oil containing enough zinc dialkyldithiophosphate (ZDTP) to give 0.1% by weight of zinc and 0.5% by weight of the test compound is placed in the test apparatus. To the above is added a catalyst package comprising 0.075 grams of oxidized fuel components, 0.075 grams of soluble metal catalyst* and 0.030 grams of water. The temperature is set at 160° C and the initial oxygen pressure is 90 psi (620 kPa). Failure is taken as the time in minutes for a pressure drop of 25 psi (172 kPa) to be observed. The test results are given below.

| Test Compound of Example | Failure Time (minutes) |
| --- | --- |
| Base oil | 99-105 |
| I | 138 |
| II | 145 |

The soluble metal catalysts are a mixture of the following metal naphthenates in the weight ratios given below: cupric 0.69%, ferric 0.41%, lead 8.0%, manganese 0.35%, stannous 0.36% (as naphthenates).

The data thus show a significant improvement in stability toward oxidation when the instant compounds are added to oil.

In summary, this invention provides a novel class of lubricant antioxidants which exhibit excellent antioxidative performance. Variations may be made in procedures, proportions and materials without departing from the scope of the invention as defined in the following claims.

What is claimed is:

1. A lubricant composition consisting essentially of a mineral oil or a synthetic oil or mixtures thereof and an effective stabilizing amount of a compound of the formula

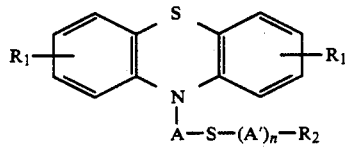

wherein
$R_1$ are independently hydrogen, alkyl of 1 to 24 carbon atoms, cycloalkyl of 5 to 7 carbon atoms or aralkyl of 7 to 9 carbon atoms;
A is methylene and A' are independently akylene of 1 to 8 carbon atoms;
n is 0 or 1; and
$R_2$ is alkyl of 1 to 18 carbon atoms, cycloalkyl of 5 to 7 carbon atoms, said cycloalkyl substituted by alkyl of 1 to 18 carbon atoms, phenyl, phenyl substituted by alkyl, alkoxy or thioalkyl to a total carbon atom content of 7 to 30, naphthyl or naphthyl substituted by alkyl, alkoxy or thioalkyl to a total carbon atom content of 11 to 40.

2. The lubricant composition of claim 1, wherein $R_1$ are independently hydrogen or alkyl of 1 to 12 carbon atoms.

3. The lubricant composition of claim 1, wherein A' is independently

wherein $R_3$ is alkyl of 1 to 7 carbon atoms.

4. The lubricant composition of claim 1, wherein $R_2$ is alkyl of 4 to 12 carbon atoms, phenyl or phenyl mono-, di- or trisubstituted by alkyl of 1 to 8 carbon atoms or one of said substitutents being alkoxy or thioalkyl of 1 to 12 carbon atoms.

5. The lubricant composition of claim 1, wherein said compound is N-(phenyliomethylene)phenothiazine.

6. The lubricant composition of claim 1, wherein said compound is N-(n-octylthiomethylene)phenothiazine.

* * * * *